US00PP17322P2

(12) United States Plant Patent
Clifford et al.

(10) Patent No.: US PP17,322 P2
(45) Date of Patent: Dec. 26, 2006

(54) ***SEDUM* PLANT NAMED 'JAWS'**

(50) Latin Name: ***Sedum* hybrid**
Varietal Denomination: Jaws

(76) Inventors: John K. Clifford, P.O. Box 473, Paw Paw, MI (US) 49079; Ken J. Clifford, P.O. Box 473, Paw Paw, MI (US) 49079

( * ) Notice: Subject to any disclaimer, the term of this patent is extended or adjusted under 35 U.S.C. 154(b) by 3 days.

(21) Appl. No.: 11/231,168

(22) Filed: Sep. 20, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Sedum, Sedum* 'Jaws', characterized by its blue-green foliage that is unique in having leaves with deep, sharp serrated margins that are cupped with curled edges. The leaves resemble shark's teeth.

2 Drawing Sheets

Botanical classification: *Sedum* hybrid.
Varietal denomination: 'Jaws'.

BACKGROUND OF THE INVENTION

The present invention relates to a new and distinct cultivar of *Sedum* of hybrid origin and will be referred to hereafter by its cultivar name, 'Jaws'. 'Jaws' was derived from *Sedum* 'Herbsfreude' (not patented), also referred to in the trade as *Sedum* 'Autumn Joy'. 'Herbsfreude' a hybrid of *Sedum telephium* and *Sedum spectabilis*.

The inventor discovered the new cultivar, 'Jaws', in a nursery in Lewisburg, Tenn. in 1999. 'Jaws' was discovered as a naturally occurring whole plant mutation as a single one gallon container found in a block of one gallon containers of 'Herbsfreude' that were originally derived from stem cuttings.

*Sedum* 'Jaws' is unique for its foliage in which the blue-green leaves have margins that are deeply and sharply serrated and are cupped and curled in orientation.

Asexual reproduction of the new cultivar was first accomplished by stem cuttings in Paw Paw, Mich. in summer of 2001 by the inventors. The new cultivar was subsequently propagated by tissue culture. The characteristics of the new cultivar have been determined to be stable and are reproduced true to type in successive generations.

SUMMARY OF THE INVENTION

The following traits have been repeatedly observed and represent the characteristics of the new cultivar as observed on plants grown for three years outdoors in Paw Paw, Mich. These attributes in combination distinguish 'Jaws' from other varieties of *Sedum* known to the inventor.

1. The leaves of 'Jaws' are deeply and sharply serrated, the parent plant, 'Herbsfreude', has leaves with margins that are smooth to finely toothed.
2. The leaves of 'Jaws' are cupped in relation to the central vein and tend to curl.
3. The foliage of 'Jaws' is blue-green with a heavy substance and waxy appearance.

BRIEF DESCRIPTION OF THE DRAWING

The plants and plant parts in the figures depict a two-year old plant of 'Jaws' as grown in a one-gallon container.

The photograph in FIG. 1 provides an overall view of 'Jaws' in bloom.

Figure 1:
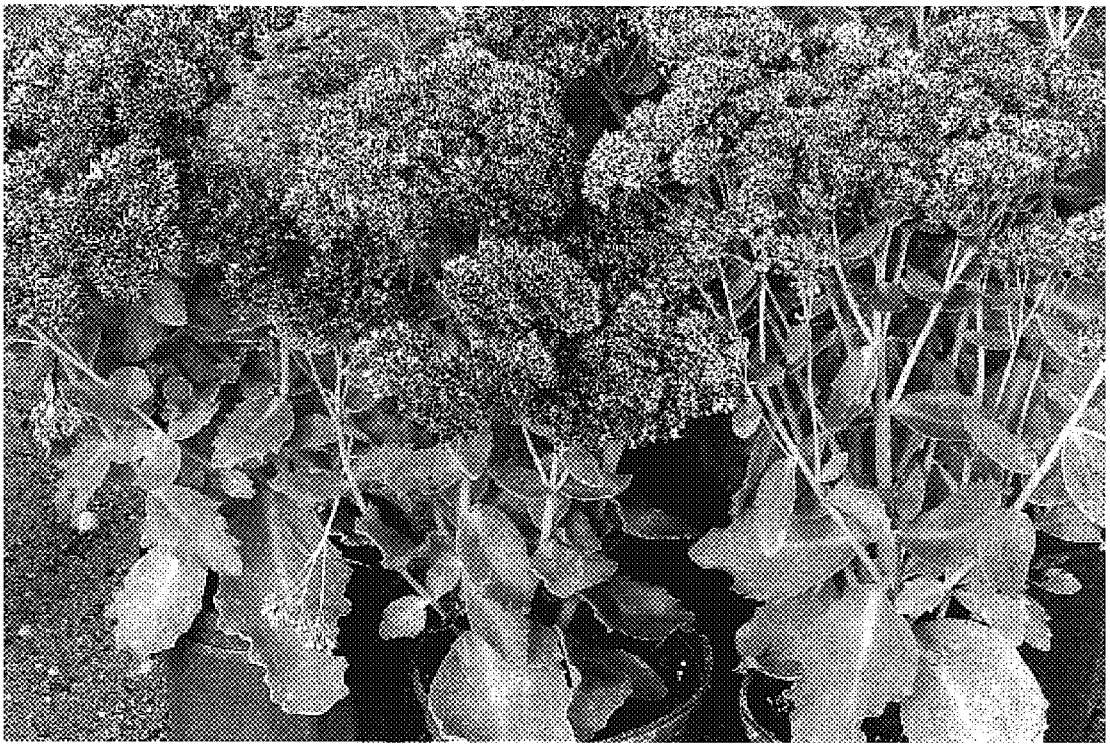
Figure 2:
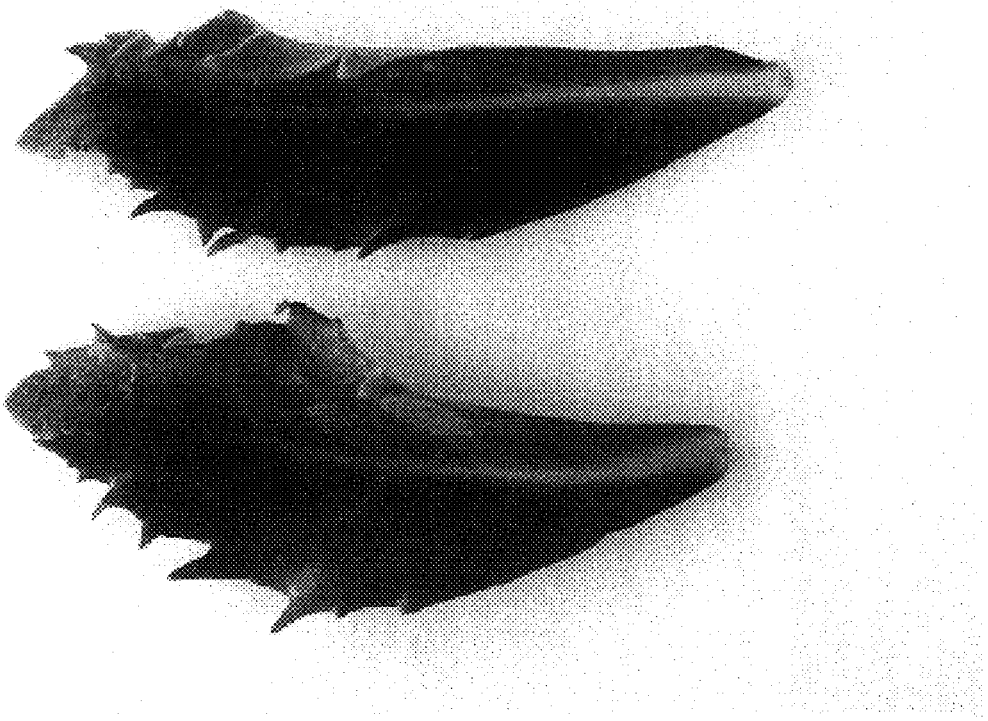

The photograph in FIG. 2 is a close up view of two typical leaves of 'Jaws'.

The colors in the photographs are as close as possible with the photographic and printing technology utilized. The color values cited in the detailed botanical description accurately describe the colors of the new *Sedum*.

DETAILED BOTANICAL DESCRIPTION

The following is a detailed description of a two year-old plant of the new cultivar as grown outdoors in a one-gallon container in full sun. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Jaws' is a cultivar of hybrid origin between *Sedum telephium* and *Sedum spectabilis*.
Parentage: Naturally occurring mutation of *Sedum* 'Herbsfreude', syn. *Sedum* 'Autumn Joy'.
General description:
- *Blooming period.*—Late summer until frost, flowers are persistent.
- *Plant habit.*—Herbaceous perennial, clump-forming, upright, all shoots arise from base, no secondary branching.
- *Growth rate.*—Vigorous growth rate.
- *Height and spread.*—About 60 cm (24 in) in height, up to about 38 cm (15 in) in width.
- *Hardiness.*—USDA Zone 3.
- *Culture.*—Prefers well-drained to moist soils in full sun to partial shade.

*Diseases and pests.*—No susceptibility or resistance to diseases or pests known to affect *Sedum* has been observed for 'Jaws'.

*Root description.*—Tap rooted with fleshy secondary roots.

Growth and propagation:

*Propagation.*—Stem cuttings and tissue culture are preferred, division is also possible.

*Root initiation.*—Terminal cutting root within 3 weeks during summer.

Stem description:

*Shape.*—Round, hollow.

*Stem color.*—145A.

*Stem size.*—Average of 1 cm in diameter, up to about 50 cm in length (including peduncle).

*Stem surface.*—Pubescent.

*Internode length.*—Average of 1.5 cm in length.

*Branching.*—Basal branches only.

Foliage description:

*Leaf shape.*—Oblanceolate.

*Leaf division.*—Simple.

*Leaf base.*—Truncate.

*Leaf apex.*—Acute.

*Leaf venation.*—Pinnate, visible but not prominent, not raised or recessed, 145A in color on upper surface, 145B in color on lower surface.

*Leaf margins.*—Deeply and sharply serrated, irregular in size, up to about 1 cm in depth and 0.6 cm in width, average of about 9 serration per side.

*Leaf attachment.*—Sessile.

*Leaf arrangement.*—Whorled, almost alternate.

*Leaf surface.*—Upper; slightly glaucous, lower; glaucous.

*Leaf color.*—Newly formed and mature: upper; intermediate between 137B and 143A, lower; intermediate between 138A and 138B.

*Leaf size.*—Size decreases in size towards apex, up to about 14 cm in length and 5.5 cm in width with an average size of 11 cm in length and 5 cm in width.

Flower description:

*Inflorescence type.*—Compound corymb of numerous star-shaped flowers.

*Flower fragrance.*—None.

*Flower type.*—Star-shaped, pistillate.

*Flower number.*—An average of about 6 compound corymbs per terminal cluster with an average of 1 to 2 lateral compound corymbs, about 60 flowers per compound corymb.

*Inflorescence size.*—Terminal clusters about 10 cm in diameter and 10 cm in depth including peduncles.

*Flower size.*—About 7 mm in depth and 4 mm in width.

*Flower color.*—Overall color is light pink due to white petals and pistils with pink apex.

*Peduncle.*—Held at about a 30° angle to stem, primary peduncles up to about 6 cm in length and 3 mm in width, secondary peduncles up to about 2 cm in length and 2 mm in width, tertiary about 1 cm in length and 1.5 mm in width. color 144A, surface is glabrous.

*Pedicel.*—Up to 4 mm in length, 0.75 mm in width, 144A in color, surface is glabrous.

*Calyx.*—Sepals 5, star-shaped, separate but fused at base.

*Sepal shape.*—Lanceolate.

*Sepal apex.*—Acute.

*Sepal size.*—2 mm in length, 0.7 mm in width.

*Sepal color.*—144A (upper and lower surface).

*Sepal surface.*—Glabrous (upper and lower surface).

*Corolla description.*—Petals 5, separate, held upward and slightly spreading.

*Petal shape.*—Lanceolate.

*Petal apex.*—Acute.

*Petal base.*—Blunt.

*Petal size.*—About 5 mm in length, 1 mm in width at base then tapering to a point at apex.

*Petal color.*—Upper and lower surface 157B (opening and fully open).

*Petal surface.*—Glabrous, both of surfaces.

*Bud shape.*—Broadly lanceolate in shape.

*Bud size.*—Up to 7 mm in length and 2 mm in width.

*Bud color.*—Newly formed; 144C Prior to opening; calyx portion 144D, petal portion 157C with tips tinged with 70C.

Reproductive organs:

*Gynoecium.*—5 Pistils, petaloid with a simple stigmatic surface, lanceolate in shape with attenuating tip, collectively flask-shaped, about 6 mm in length and 1.5 mm in width, apex is 70B in color with a base of 157A. Ovules comprised of a tiny scale at the base of each carp, inferior, 0.5 mm in diameter, 144D in color.

*Androcoecium.*—No stamens present, male sterile.

*Fruit/seed.*—No seed production was observed, sterile.

We claim:

1. A new and distinct cultivar of *Sedum* plant named 'Jaws' as herein illustrated and described.

* * * * *